United States Patent
Nishiyama et al.

(10) Patent No.: US 11,219,404 B2
(45) Date of Patent: Jan. 11, 2022

(54) COGNITIVE DECLINE DETECTION SYSTEM

(71) Applicant: PANASONIC INTELLECTUAL PROPERTY MANAGEMENT CO., LTD., Osaka (JP)

(72) Inventors: Takashi Nishiyama, Hyogo (JP); Yoshihiro Matsumura, Osaka (JP); Kengo Abe, Nara (JP)

(73) Assignee: PANASONIC INTELLECTUAL PROPERTY MANAGEMENT CO, LTD., Osaka (JP)

( * ) Notice: Subject to any disclaimer, the term of this patent is extended or adjusted under 35 U.S.C. 154(b) by 0 days.

(21) Appl. No.: 16/769,462

(22) PCT Filed: Nov. 19, 2018

(86) PCT No.: PCT/JP2018/042620
§ 371 (c)(1),
(2) Date: Jun. 3, 2020

(87) PCT Pub. No.: WO2019/116830
PCT Pub. Date: Jun. 20, 2019

(65) Prior Publication Data
US 2021/0186410 A1    Jun. 24, 2021

(30) Foreign Application Priority Data
Dec. 13, 2017  (JP) .............................. JP2017-238903

(51) Int. Cl.
*A61B 5/00* (2006.01)
*G16H 40/67* (2018.01)
(Continued)

(52) U.S. Cl.
CPC .......... *A61B 5/4088* (2013.01); *A61B 5/1118* (2013.01); *A61B 5/4809* (2013.01);
(Continued)

(58) Field of Classification Search
CPC ..... A61B 5/389; A61B 5/6844; A61B 5/6843; A61B 5/4094; A61B 5/276
See application file for complete search history.

(56) References Cited

U.S. PATENT DOCUMENTS

2017/0156680 A1* 6/2017 Barretto ............... A61B 5/0022

FOREIGN PATENT DOCUMENTS

| JP | 2001-258859 A | 9/2001 |
|----|---------------|--------|
| JP | 2004-046560 A | 2/2004 |

(Continued)

OTHER PUBLICATIONS

International Search Report and Written Opinion dated Feb. 5, 2019 in International Application No. PCT/JP2018/042620; with partial English translation.

*Primary Examiner* — Sean P Dougherty
*Assistant Examiner* — Alexander H Connor
(74) *Attorney, Agent, or Firm* — McDermott Will and Emery LLP

(57) ABSTRACT

Cognitive decline detection system includes obtainment unit and determination unit. Obtainment unit obtains the amount of movement during a sleep period and the amount of movement during a non-sleep period of a user for each day, the non-sleep period being the period other than the sleep period. Determination unit determines that the cognitive function of the user is lower during a determination period than during a comparison period set before the determination period when the frequency of days when a movement amount ratio falls below a predetermined ratio among days constituting the determination period is higher than that among days constituting the comparison period, the movement amount ratio representing the ratio of the amount of movement during the non-sleep period to the amount of movement during the sleep period.

8 Claims, 8 Drawing Sheets

(51) Int. Cl.
*G16H 20/70* (2018.01)
*A61B 5/11* (2006.01)
(52) U.S. Cl.
CPC ........... *A61B 5/7282* (2013.01); *G16H 20/70* (2018.01); *G16H 40/67* (2018.01)

(56) References Cited

FOREIGN PATENT DOCUMENTS

| JP | 2015-215711 | A | 12/2015 |
| JP | 2016-022310 | A | 2/2016 |
| JP | 5901089 | B1 | 4/2016 |
| JP | 2016-144560 | A | 8/2016 |

\* cited by examiner

COGNITIVE DECLINE DETECTION SYSTEM

CROSS-REFERENCE OF RELATED APPLICATIONS

This application is the U.S. National Phase under 35 U.S.C. § 371 of International Patent Application No. PCT/JP2018/042620, filed on Nov. 19, 2018, which in turn claims the benefit of Japanese Application No. 2017-238903, filed on Dec. 13, 2017, the entire disclosures of which Applications are incorporated by reference herein.

TECHNICAL FIELD

The present invention relates to, for example, a cognitive decline detection system for detecting cognitive decline.

BACKGROUND ART

Patent Literature 1 discloses a dementia risk detection system for detecting a risk of dementia. Specifically, the dementia risk detection system generates the sleep data of a subject tested by the system from the sleep-time biological data of the subject and compares the sleep data of the subject with sleep data representing various conditions to detect a risk of dementia. According to Patent Literature 1, the dementia risk detection system can detect a potential risk of dementia at a very early stage and thus contribute to prevention of dementia to delay the onset of dementia.

CITATION LIST

Patent Literature

PTL 1: Japanese Unexamined Patent Application Publication No. 2016-022310

SUMMARY OF THE INVENTION

Technical Problem

However, it may be difficult to properly detect cognitive decline only from the sleep-time data of a subject.

Thus, the present invention aims to provide, for example, a cognitive decline detection system capable of properly detecting cognitive decline.

Solutions to Problem

A cognitive decline detection system according to one aspect of the present invention includes: an obtainment unit that obtains the amount of movement during a sleep period and the amount of movement during a non-sleep period of a user for each day, the non-sleep period being the period other than the sleep period; and a determination unit that determines that the cognitive function of the user is lower during a determination period than during a comparison period set before the determination period when the frequency of days when a movement amount ratio falls below a predetermined ratio among days constituting the determination period is higher than the frequency of days when the movement amount ratio falls below the predetermined ratio among days constituting the comparison period, the movement amount ratio representing the ratio of the amount of movement during the non-sleep period to the amount of movement during the sleep period.

A cognitive decline detection system according to another aspect of the present invention may include: an obtainment unit that obtains the amount of movement during a sleep period and the amount of movement during a non-sleep period of a user for each day, the non-sleep period being the period other than the sleep period; and a determination unit that determines that the user has experienced a decline in cognitive function during a determination period when the value of the slope of an approximation straight line falls below a predetermined value of a slope, the approximation straight line being obtained for a ratio change represented by movement amount ratios for the respective days of the determination period, and the movement amount ratios each representing the ratio of the amount of movement during the non-sleep period to the amount of movement during the sleep period.

A non-transitory computer-readable recording medium according to another aspect of the present invention is a non-transitory computer-readable recording medium for use in a computer, the recording medium having a computer program recorded thereon for causing the computer to perform a cognitive decline detection method. The cognitive decline detection method includes: obtaining the amount of movement during a sleep period and the amount of movement during a non-sleep period of a user for each day, the non-sleep period being the period other than the sleep period; and determining that the cognitive function of the user is lower during a determination period than during a comparison period set before the determination period when the frequency of days when a movement amount ratio falls below a predetermined ratio among days constituting the determination period is higher than the frequency of days when the movement amount ratio falls below the predetermined ratio among days constituting the comparison period, the movement amount ratio representing the ratio of the amount of movement during the non-sleep period to the amount of movement during the sleep period.

A non-transitory computer-readable recording medium according to another aspect of the present invention may be a non-transitory computer-readable recording medium for use in a computer, the recording medium having a computer program recorded thereon for causing the computer to perform a cognitive decline detection method. The cognitive decline detection method includes: obtaining the amount of movement during a sleep period and the amount of movement during a non-sleep period of a user for each day, the non-sleep period being the period other than the sleep period; and determining that the user has experienced a decline in cognitive function during a determination period when the value of the slope of an approximation straight line falls below a predetermined value of a slope, the approximation straight line being obtained for a ratio change represented by movement amount ratios for the respective days of the determination period, and the movement amount ratios each representing the ratio of the amount of movement during the non-sleep period to the amount of movement during the sleep period.

Advantageous Effect of Invention

A cognitive decline detection system or a non-transitory computer-readable recording medium according to an aspect of the present invention can properly detect cognitive decline.

DESCRIPTION OF EXEMPLARY EMBODIMENT (Underlying Knowledge Forming the Basis of the Present Disclosure)

In the aging society, problems involving elderly people with dementia are more likely to come to the surface. These days, the media frequently reports car accidents caused by elderly drivers with dementia who, for example, drove the wrong way on an expressway or drove on a sidewalk, and TV programs related to dementia are repeatedly broadcast.

Dementia involves various stages ranging from a mild stage to a severe stage. If an abnormality is found at the stage of mild cognitive impairment (MCI) before the onset of dementia, it may be possible to suppress development of dementia by, for example, getting exercise. Thus, there is growing interest in early detection of an abnormality at the stage of mild cognitive impairment. However, it is not easy to detect an abnormality at an early stage, and an abnormality may be overlooked.

It is known that an abnormality can be found in a subject at an early stage by the subject themselves finding an abnormality or by people around the subject finding an abnormality. In the latter case, the people around the subject find an abnormality in the way the subject talks or in the living activities of the subject. Here, the case is described in which the people around the subject find an abnormality in the living activities of the subject.

Specifically, the subject who has developed Alzheimer's dementia may suffer from circadian rhythm sleep disorders, which result in, for example, the decreased daytime-activity level of the subject. Thus, the subject may doze off even during the daytime and have light sleep during the night-time.

Specifically, patients with dementia may have severe organic dysfunction in large areas of the hypothalamus and brainstem that control their biological clocks associated with, for example, sleep and waking states. In particular, in patients with Alzheimer's dementia, daily sleep time is divided into multiple portions, and sleep may frequently alternate with waking states during the night-time on a daily basis.

Figure 1A:
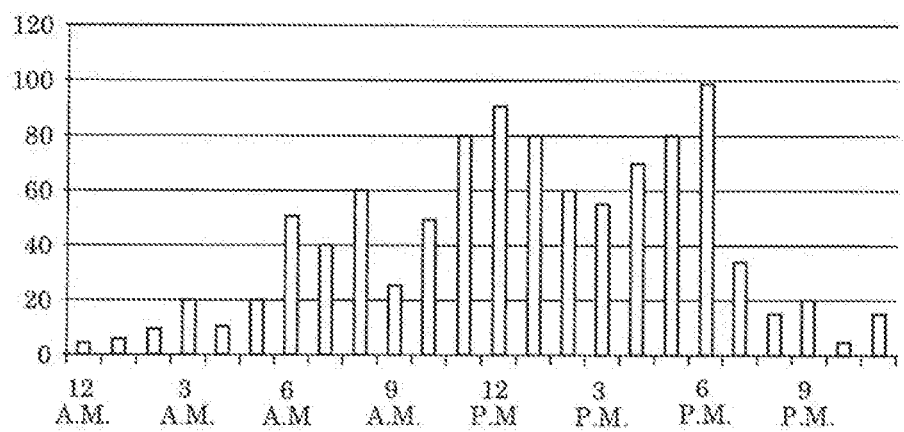
FIG. 1A is a graph illustrating the amount of movement for one day of an elderly person without dementia.
Figure 1B:
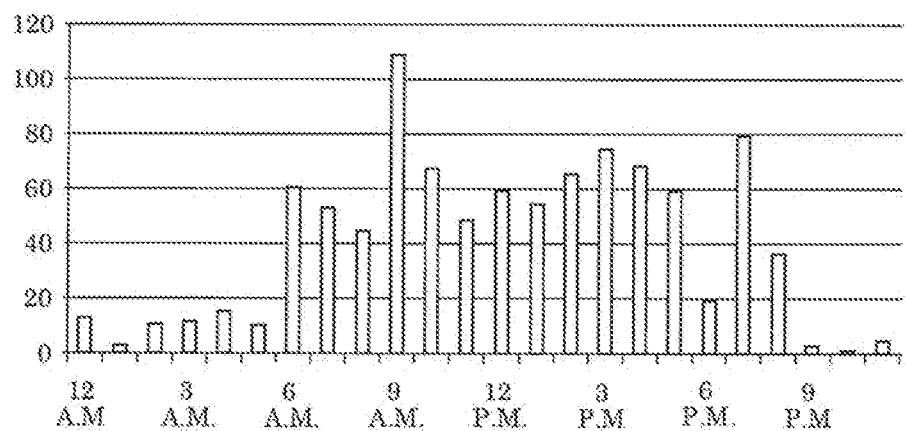
FIG. 1B is a graph illustrating the amount of movement for the next day of the elderly person without dementia.

FIGS. 1A and 1B are graphs schematically illustrating the amount of movement for each hour of an elderly person without dementia, for two consecutive days. Specifically, FIG. 1A schematically illustrates the amount of movement for each hour of the elderly person without dementia, for the first day of the two consecutive days. FIG. 1B schematically illustrates the amount of movement for each hour of the elderly person without dementia, for the second day of the two consecutive days. To obtain the amounts of movement illustrated in FIGS. 1A and 1B, a sensor measures amounts of movement at one-minute intervals and rates each of the amounts of movement on a scale of 0 to 9 according to the magnitude of movement, and numerical values assigned to the respective amounts of movement are accumulated for each hour.

For the elderly person without dementia, as illustrated in FIGS. 1A and 1B, there is a clear difference between the amount of movement during the daytime activity period and the amount of movement during the night-time sleep period.

Figure 2A:
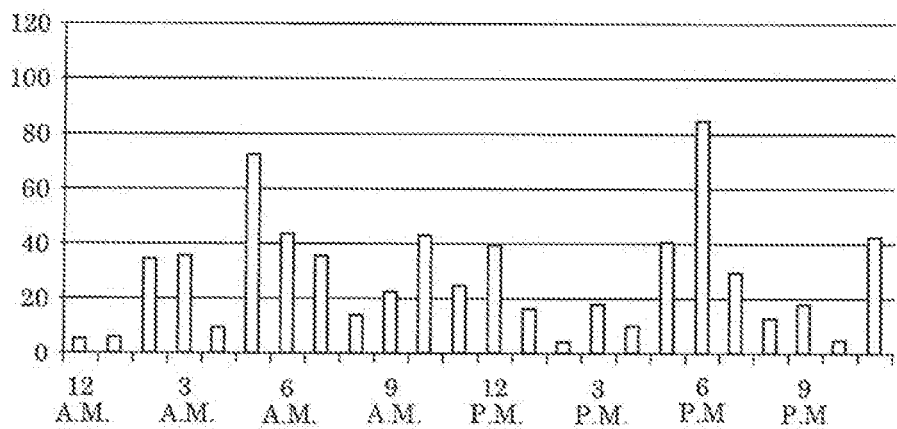
FIG. 2A is a graph illustrating the amount of movement for one day of an elderly person with dementia.
Figure 2B:
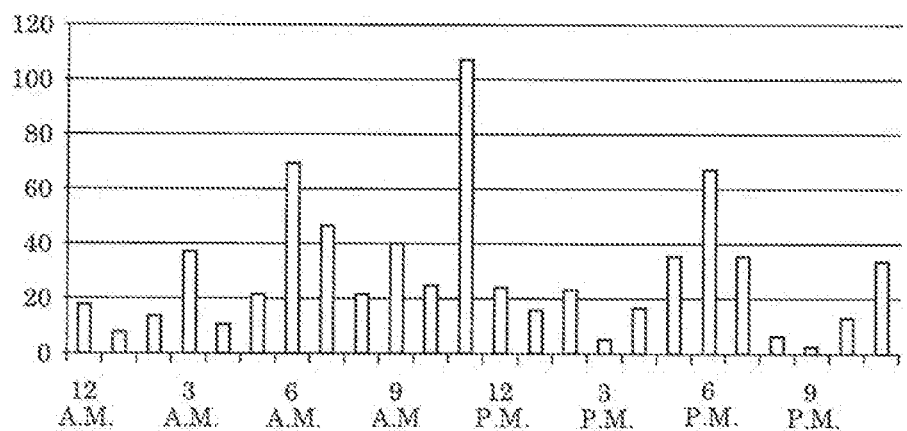
FIG. 2B is a graph illustrating the amount of movement for the next day of the elderly person with dementia.

FIGS. 2A and 2B are graphs schematically illustrating the amount of movement for each hour of an elderly person with dementia, for two consecutive days. Specifically, FIG. 2A schematically illustrates the amount of movement for each hour of the elderly person with dementia, for the first day of the two consecutive days. FIG. 2B schematically illustrates the amount of movement for each hour of the elderly person with dementia, for the second day of the two consecutive days. To obtain the amounts of movement illustrated in FIGS. 2A and 2B, as in the case of the amounts of movement illustrated in FIGS. 1A and 1B, a sensor measures amounts of movement at one-minute intervals and rates each of the amounts of movement on a scale of 0 to 9 according to the magnitude of movement, and numerical values assigned to the respective amounts of movement are accumulated for each hour.

For the elderly person with dementia, as illustrated in FIGS. 2A and 2B, there is an unclear difference between the amount of movement during the daytime activity period and the amount of movement during the night-time sleep period. That is, the subject who has developed dementia may doze off during the daytime and thus wake up during the night-time. In addition, a state continues in which it is difficult to forecast what time during the daytime the subject will doze off and what time during the night-time the subject will wake up. Then, getting-up time in the morning, nap time, and bedtime at night vary, and consequently their daily life pattern may be rendered unstable.

Technical ideas for a cognitive decline detection system came from, for example, the underlying knowledge set forth above, the cognitive decline detection system being capable of detecting cognitive decline in accordance with the ratio of the amount of movement during the non-sleep period to the amount of movement during the sleep period. Hereinafter, an embodiment of the cognitive decline detection system is described with reference to the Drawings.

The embodiment described herein is intended to explain a specific example of the present invention. Thus, the numerical values, the shapes, the materials, the structural elements, the positions of the structural elements, the connections between the structural elements, the steps, the order of the steps, and others disclosed in the embodiment are mere examples and are not intended to limit the present invention. In addition, among the structural elements described in the embodiment, the structural elements not recited in the independent claims are structural elements that can be optionally added.

The drawings are schematically drawn and not necessarily precisely drawn. In particular, the values illustrated in the graphs may not be accurate.

Embodiment

Figure 3:
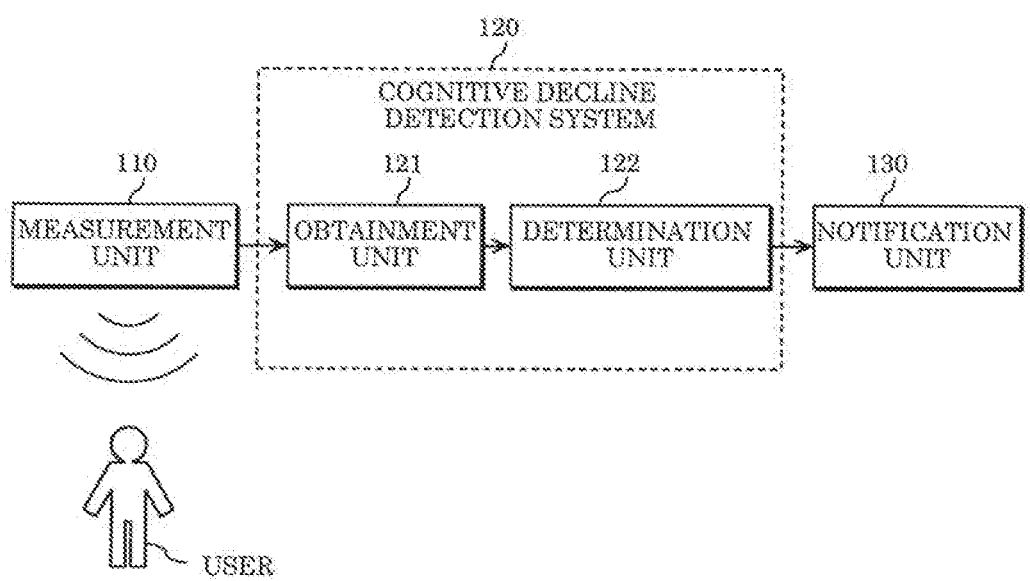
FIG. 3 is a block diagram illustrating a configuration of a cognitive decline detection system and other devices in an embodiment.

FIG. 3 is a block diagram illustrating a configuration of a cognitive decline detection system and other devices in an embodiment. Cognitive decline detection system 120 in FIG. 3 includes obtainment unit 121 and determination unit 122. In addition, FIG. 3 illustrates measurement unit 110 and notification unit 130.

For instance, various information is transmitted from measurement unit 110 to obtainment unit 121, from obtainment unit 121 to determination unit 122, and from determination unit 122 to notification unit 130 via, for example, an input and output circuit, a communication line, or a communication network. For communication for transmitting information, wired or wireless communication may be used.

Measurement unit 110 is a measurement device for measuring the amount of movement of a user and may be also referred to as movement sensor. Measurement unit 110 may be made of an electric circuit. To measure the amount of movement of a user, measurement unit 110 may be carried by the user or set in a space used by the user. Alternatively, measurement unit 110 may include more than one structural element, and a part of the structural elements may be carried by the user or set in the space used by the user.

For instance, measurement unit 110 may include a vibration detector carried by the user. As the amount of movement of the user, measurement unit 110 may measure the amount of vibration received by the vibration detector. Instead of being carried by the user, the vibration detector may be placed on, for example, the bed of the user.

In addition, measurement unit 110 may include a camera set in the room of the user. In accordance with video obtained from the camera, measurement unit 110 may measure the amount of movement contained in the video as the amount of movement of the user.

In addition, measurement unit 110 may include a transmit-receive antenna set in the room of the user. For instance, the transmit-receive antenna transmits an electromagnetic wave and receives the reflected wave of the electromagnetic wave. Measurement unit 110 may measure the amount of movement in accordance with a difference between the waveform of the transmitted electromagnetic wave and the waveform of the received reflected wave. Specifically, in this instance, Doppler's principle may be used.

Moreover, measurement unit 110 may measure an amount of movement in combination of the vibration detector, the camera, the transmit-receive antenna, and other devices.

Moreover, for instance, measurement unit 110 measures amounts of movement at one-minute intervals and rates each of the amounts of movement on a scale of 0 to 9. The larger the amount of movement, the larger the numerical value. When the user is not moving, the amount of movement indicates 0.

Obtainment unit 121 is an information processing unit for obtaining the amount of movement during a sleep period and the amount of movement during a non-sleep period of the user for each day. Obtainment unit 121 may be made of an electric circuit. It should be noted that the non-sleep period is the period other than the sleep period. The period other than the sleep period may be also referred to as active period. The amount of movement during the non-sleep period may be also referred to as the amount of movement during the active period.

For instance, obtainment unit 121 obtains, from measurement unit 110, the amounts of movement measured at one-minute intervals by measurement unit 110. Then, obtainment unit 121 separates the amounts of movement measured at one-minute intervals into the amount of movement during the sleep period and the amount of movement during the non-sleep period, which are then accumulated for each day. Thus, obtainment unit 121 obtains the amount of movement during the sleep period and the amount of movement during the non-sleep period for each day.

The sleep period and the non-sleep period may be identified in accordance with the amounts of movement measured at one-minute intervals. For instance, when the state in which the amount of movement indicates 0 continues for 30 minutes or more, obtainment unit 121 may identify the time point when the state starts as falling-asleep time. Moreover, when the state in which the amount of movement indicates 1 or greater continues for 30 minutes or more, obtainment unit 121 may identify the time point when the state starts as getting-up time. Then, obtainment unit 121 may identify the period from the falling-asleep time to the getting-up time as the sleep period and identify the other period as the non-sleep period.

In addition, for instance, a time period from which falling-asleep time is identified and a time period from which getting-up time is identified may be preset. Specifically, when the state in which the amount of movement indicates 0 continues for 30 minutes or more from 10 p.m. to 1 a.m., during which the user is likely to fall asleep, obtainment unit 121 may identify the time point when the state starts as falling-asleep time. Likewise, when the state in which the amount of movement indicates 1 or greater continues for 30 minutes or more from 5 a.m. to 8 a.m., during which the user is likely to get up, obtainment unit 121 may identify the time point when the state starts as getting-up time.

Alternatively, falling-asleep time and getting-up time may be preset. That is, the sleep-period and the non-sleep period may be preset. For instance, the sleep period may be preset to the period from 11 p.m. to 6 a.m., and the non-sleep period may be preset to the period from 6 a.m. to 11 p.m. Moreover, the sleep period and the non-sleep period may be identified in accordance with, for example, information reported by the user or care records.

Obtainment unit 121 then accumulates the amount of movement during the sleep period for each day in accordance with the amounts of movement measured at one-minute intervals to obtain the amount of movement during the sleep period for each day. Obtainment unit 121 accumulates the amount of movement during the non-sleep period for each day in accordance with the amounts of movement measured at one-minute intervals to obtain the amount of movement during the non-sleep period for each day.

Determination unit 122 is an information processing unit for determining whether the user has experienced cognitive decline. Determination unit 122 may be made of an electric circuit. Determination unit 122 determines whether the user has experienced cognitive decline, in accordance with the amount of movement during the sleep period and the amount of movement during the non-sleep period obtained by obtainment unit 121. More specifically, determination unit 122 determines whether the user has experienced cognitive decline, in accordance with the movement amount ratio representing the ratio of the amount of movement during the non-sleep period to the amount of movement during the sleep period.

Cognitive function is intellectual function related to perception, comprehension, and judgment. The user who has developed dementia or mild cognitive impairment experiences cognitive decline. In addition, due to the occurrence of circadian rhythm sleep disorders caused by cognitive decline, the amount of movement during the daytime is likely to decrease, and the amount of movement during the night-time is likely to increase. Thus, due to the occurrence of the circadian rhythm sleep disorders caused by cognitive decline, the ratio of the amount of movement during the non-sleep period to the amount of movement during the sleep period is likely to decrease.

Meanwhile, activities of the user vary from day to day. Thus, even if the user has experienced no cognitive decline, the movement amount ratio may decline, depending on the day. That is, it is difficult to properly detect cognitive decline in accordance with the movement amount ratio for one day.

Thus, for instance, determination unit 122 calculates the ratio of the amount of movement during the non-sleep period to the amount of movement during the sleep period for each day. Then, determination unit 122 determines, for each day, whether the movement amount ratio falls below a predetermined ratio. In accordance with the frequency of days when the movement amount ratio falls below the predetermined ratio, determination unit 122 determines whether the user has experienced cognitive decline.

A day when the movement amount ratio falls below the predetermined ratio is also referred to as not good day. The frequency of not good days during a predetermined period may be indicated by the proportion of the number of not good days to the total number of days of the predetermined period or the number of consecutive not good days during the predetermined period.

Moreover, for instance, determination unit 122 determines whether the frequency of not good days is higher during a determination period than during a comparison period, which is before the determination period. When the frequency of not good days is higher during the determination period than during the comparison period, determination unit 122 determines that the cognitive function of the user is lower during the determination period than during the comparison period.

As a more specific instance, when the frequency of not good days in August, which is the determination period, is higher than that in July, which is the comparison period, determination unit 122 may determine that the cognitive function of the user is lower in August than in July.

In addition, the determination period and the comparison period may overlap each other. For instance, a case in which the determination period comes after the comparison period may include the case in which the final day of the determination period is after the final day of the comparison period. Specifically, while extending the determination period for one day each day, determination unit 122 may determine whether the cognitive function of the user is lower during a current determination period than during a previous determination period.

Moreover, the predetermined ratio may be based on the past movement amount ratios of the user. For instance, the predetermined ratio may be based on the movement amount ratios of the user for a reference period, which is before the comparison period. Specifically, the predetermined ratio may be set in accordance with a statistic derived from the movement amount ratios of the user for the respective days of the reference period, which is before the comparison period. More specifically, the predetermined ratio may be the mean value of the movement amount ratios or a value derived by subtracting the standard deviation of the movement amount ratios from the mean value of the movement amount ratios.

Here, the standard deviation of the movement amount ratios is equivalent to the square root of the mean of the squares of deviations derived by subtracting the mean value of the movement amount ratios from each of the movement amount ratios.

It should be noted that the reference period is a period, for example, during which it is acknowledged that the user stays healthy. In addition, the determination period for which cognitive decline has not been detected may be used as the reference period for the following period. For instance, when it is not determined that the cognitive function of the user is lower in June than in May, a new predetermined ratio may be set in accordance with the movement amount ratios in June and used as the predetermined ratio for deriving the frequency of not good days in July or August.

Moreover, determination unit 122 may determine whether the frequency of not good days during the comparison period is higher than a predetermined frequency. Then, determination unit 122 may determine whether the frequency of not good days during the determination period is higher than the predetermined frequency. When the frequency of not good days during the comparison period is not higher than the predetermined frequency, and the frequency of not good days during the determination period is higher than the predetermined frequency, determination unit 122 may determine that the cognitive function of the user is lower during the determination period than during the comparison period.

Thus, according to whether the frequency of not good days increases to an abnormally high frequency, determination unit 122 may determine whether the cognitive function of the user decreases to abnormally low cognitive function.

It should be noted that the predetermined frequency may be determined in accordance with the frequency of not good days during a past period. The past period may be the reference period. Alternatively, the predetermined frequency may be set in accordance with a statistic derived from the frequency of not good days for each of reference periods. Specifically, the predetermined frequency may be the mean value of the frequencies of not good days or a value derived by subtracting the standard deviation of the movement amount ratios from the mean value of the frequencies of not good days.

Notification unit 130 is a notification device for indicating cognitive decline. Notification unit 130 may be made of an electric circuit. Notification unit 130 may be an information processing terminal. More specifically, notification unit 130 may be a cellular phone, a smartphone, a tablet device, or a personal computer. For instance, notification unit 130 may be carried by the caregiver of the user or set in a space used by the caregiver of the user.

When determination unit 122 detects cognitive decline in the user, notification unit 130 indicates cognitive decline in the user. For instance, when detecting cognitive decline in the user, determination unit 122 transmits, to notification unit 130, determination result information indicating cognitive decline in the user. Notification unit 130 receives the determination result information indicating cognitive decline in the user and indicates cognitive decline in the user in accordance with the determination result information.

Notification unit 130 may include a display. By causing the display to display the information indicating cognitive decline in the user, notification unit 130 may indicate cognitive decline in the user. In addition, notification unit 130 may include a speaker. By causing the speaker to output the sound of the information indicating cognitive decline in the user, notification unit 130 may indicate cognitive decline in the user.

As discussed above, cognitive decline detection system 120 includes obtainment unit 121 and determination unit 122. Cognitive decline detection system 120 is, for example, a computer system including a processor and memory. Obtainment unit 121 and determination unit 122 may be caused to function by the processor, the memory, and other components.

Moreover, cognitive decline detection system 120 may be one device or be made up of more than one device. Cognitive decline detection system 120 may be set in the space used by the user, the space used by the caregiver of the user, or other space. In the embodiment, cognitive decline detection system 120 determines whether a user has experienced cognitive decline. However, cognitive decline detection system 120 may determine whether each of more than one user has experienced cognitive decline.

Cognitive decline detection system 120 may further include measurement unit 110 and notification unit 130. In addition, cognitive decline detection system 120 may include measurement unit 110 for each user and include notification unit 130 for each caregiver.

Figure 4:
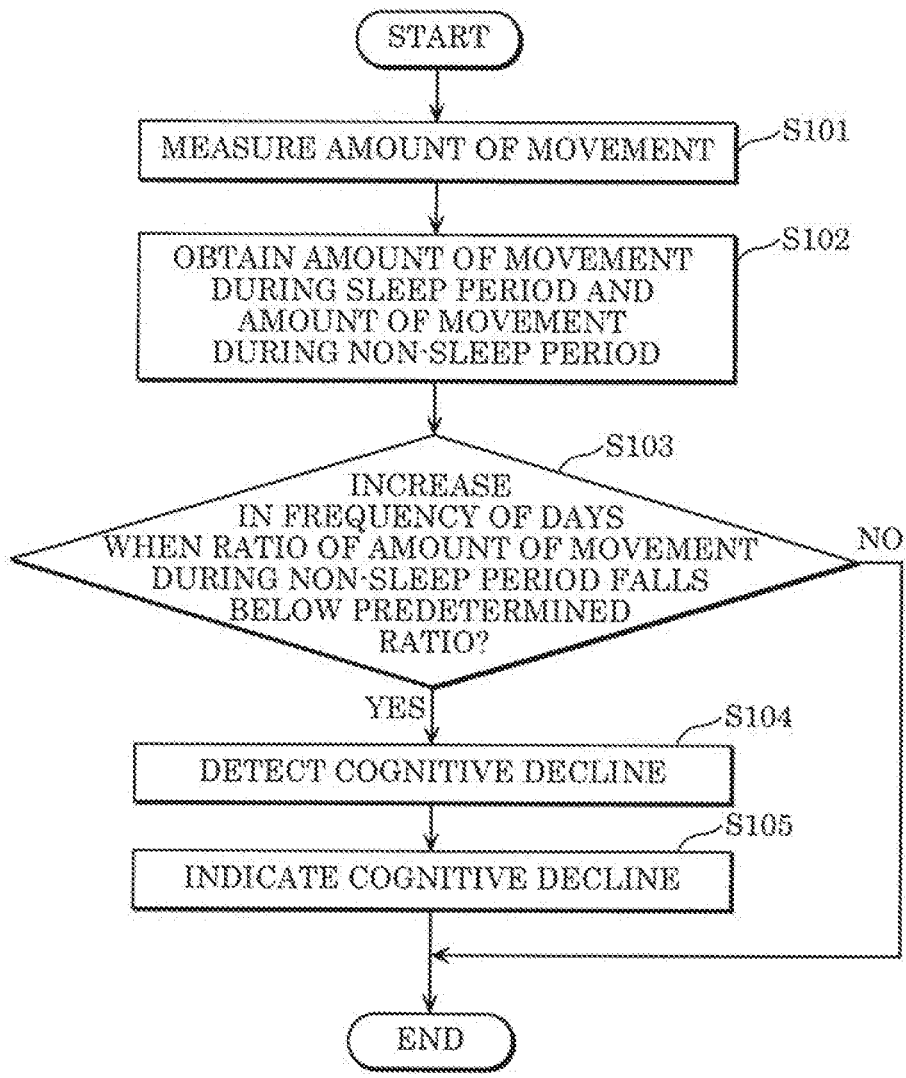
FIG. 4 is a flowchart illustrating operation of the cognitive decline detection system and the other devices in the embodiment.

FIG. 4 is a flowchart illustrating operation of cognitive decline detection system 120 and other devices in the embodiment.

Measurement unit 110 measures the amount of movement of the user (S101). For instance, measurement unit 110 measures the amounts of movement of the user at one-minute intervals.

Obtainment unit 121 obtains the amount of movement during the sleep period and the amount of movement during the non-sleep period (S102). For instance, obtainment unit 121 separates the amounts of movement measured at one-minute intervals into the amount of movement during the sleep period and the amount of movement during the non-sleep period, which are then accumulated for each day. Thus, obtainment unit 121 obtains the amount of movement during the sleep period and the amount of movement during the non-sleep period for each day.

Determination unit 122 determines whether there is an increase in the frequency of days when the ratio of the amount of movement during the non-sleep period to the amount of movement during the sleep period falls below the predetermined ratio (S103). That is, determination unit 122 determines whether the frequency of not good days is higher during the determination period than during the comparison period, which is before the determination period.

When there is an increase in the frequency of days when the ratio of the amount of movement during the non-sleep period to the amount of movement during the sleep period falls below the predetermined ratio (Yes in S103), determination unit 122 detects cognitive decline (S104). That is, when the frequency of not good days is higher during the determination period than during the comparison period, determination unit 122 determines that the cognitive function of the user is lower during the determination period than during the comparison period.

When there is an increase in the frequency of days when the ratio of the amount of movement during the non-sleep period to the amount of movement during the sleep period falls below the predetermined ratio (Yes in S103), notification unit 130 indicates cognitive decline (S105). That is, when the frequency of not good days is higher during the determination period than during the comparison period, notification unit 130 indicates that the cognitive function of the user is lower during the determination period than during the comparison period.

In the above operation, cognitive decline detection system 120 can properly detect cognitive decline, in accordance with the frequency of days when the ratio of the amount of movement during the non-sleep period to the amount of movement during the sleep period falls below the predetermined ratio.

It should be noted that when there is no increase in the frequency of days when the movement amount ratio falls below the predetermined ratio (No in S103), determination unit 122 may determine that the user has experienced no cognitive decline. In this instance, notification unit 130 may indicate that the user has experienced no cognitive decline.

Moreover, in the above operation, the condition of whether the ratio of the amount of movement during the non-sleep period to the amount of movement during the sleep period falls below the predetermined ratio is used. By using other condition substantially the same as the condition, the condition of whether the ratio of the amount of movement during the non-sleep period to the amount of movement during the sleep period falls below the predetermined ratio may be used.

Specifically, by using the condition of whether the ratio of the amount of movement during the non-sleep period to the total of the amount of movement during the sleep period and the amount of movement during the non-sleep period falls below a predetermined threshold, the condition of whether the ratio of the amount of movement during the non-sleep period to the amount of movement during the sleep period falls below the predetermined ratio may be used. Alternatively, by using the condition of whether the ratio of the amount of movement during the sleep period to the amount of movement during the non-sleep period is higher than a predetermined threshold, the condition of whether the ratio of the amount of movement during the non-sleep period to the amount of movement during the sleep period falls below the predetermined ratio may be used.

As discussed above, the sleep period and the non-sleep period may be identified in accordance with the amounts of movement measured by measurement unit 110.

Figure 5:
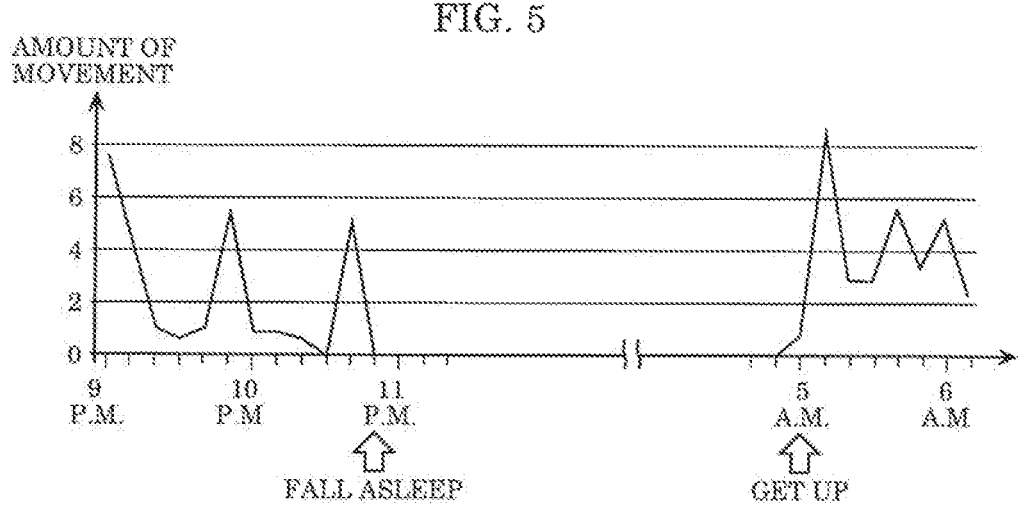
FIG. 5 is a graph illustrating a temporal change in the amount of movement.

FIG. 5 is a graph illustrating a temporal change in the amount of movement. For instance, the state in which the amount of movement indicates 0 continues for 30 minutes or more from 10.50 p.m. Thus, obtainment unit 121 may identify 10.50 p.m. as falling-asleep time. In addition, the state in which the amount of movement indicates 1 or greater continues for 30 minutes or more from 5 a.m. Thus, obtainment unit 121 may identify 5 a.m. as getting-up time.

It should be noted that in the above instance, 30-minutes-or-more continuation of the state in which the amount of movement indicates 0 and 30-minutes-or-more continuation of the state in which the amount of movement indicates 1 or greater are used as conditions. However, such numerical values are mere examples and may be appropriately changed. In addition, the method of identifying falling-asleep time and getting-up time is a mere example and is not limited to the example. As discussed above, falling-asleep time and getting-up time may be preset.

Figure 6:
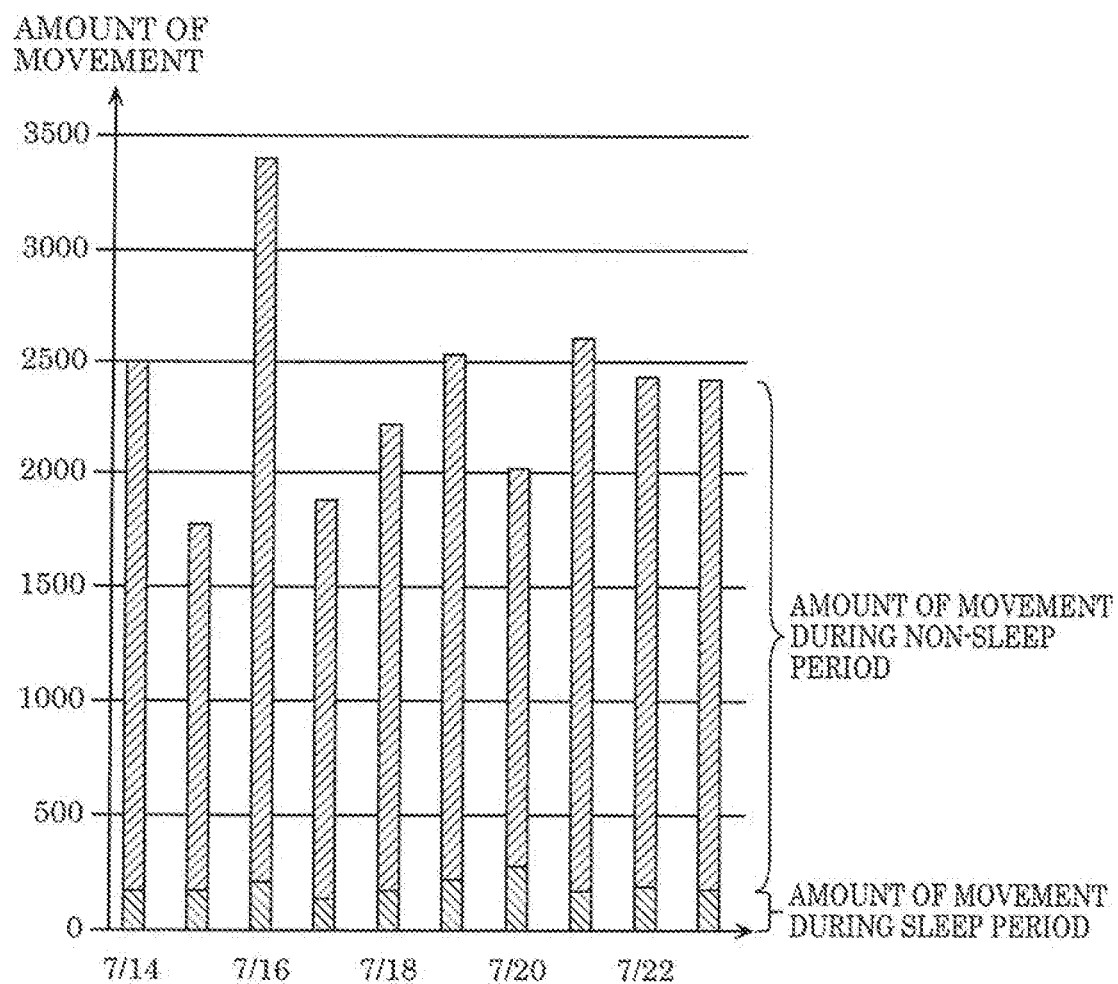
FIG. 6 is a graph illustrating the amount of movement during a sleep period and the amount of movement during a non-sleep period for each day.

FIG. 6 is a graph illustrating the amount of movement during the sleep period and the amount of movement during the non-sleep period for each day. FIG. 6 illustrates the amount of movement during the sleep period and the amount of movement during the non-sleep period in different hatching patterns for each of the 10 days from July 14th to July 23rd. The lower portion of each bar in the graph denotes the amount of movement during the sleep period, and the upper portion of each bar denotes the amount of movement during the non-sleep period. Obtainment unit 121 obtains amounts of movement during the sleep period and amounts of movement during the non-sleep period as illustrated in FIG. 6.

Figure 7:
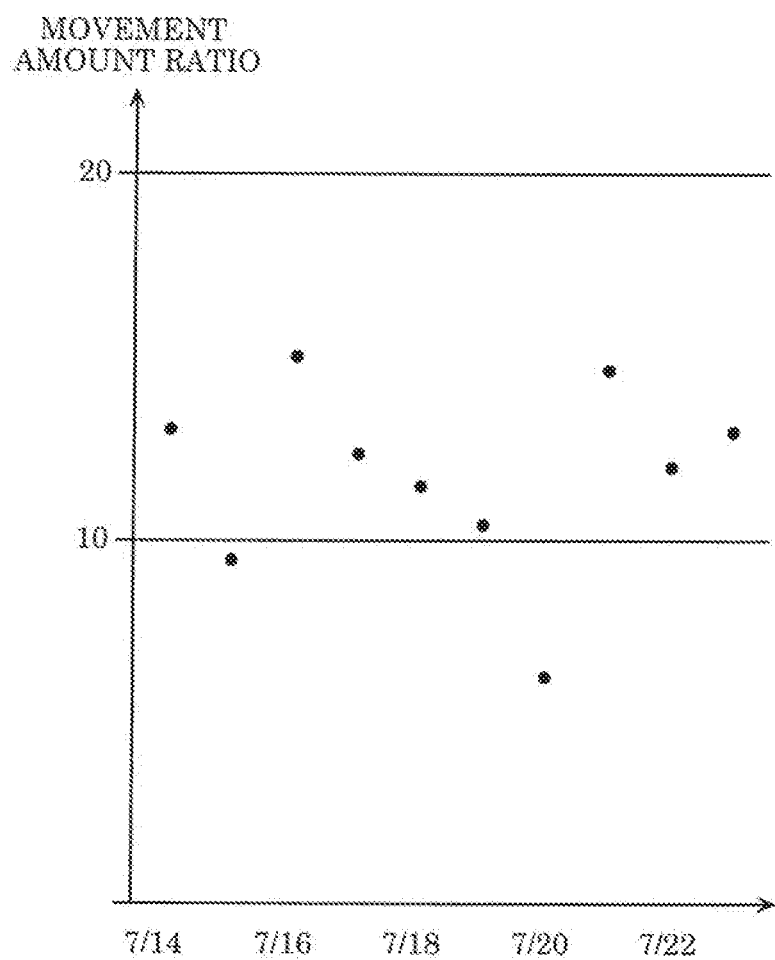
FIG. 7 is a graph illustrating the ratio of the amount of movement during the non-sleep period to the amount of movement during the sleep period for each day.

FIG. 7 is a graph illustrating the ratio of the amount of movement during the non-sleep period to the amount of movement during the sleep period for each day. The movement amount ratio is calculated by dividing the amount of movement during the non-sleep period by the amount of movement during the sleep period. In FIG. 7, movement amount ratios calculated for the respective 10 days from July 14th to July 23rd are plotted. Determination unit 122 may obtain movement amount ratios as illustrated in FIG. 7. Then, determination unit 122 derives the frequency of days when the movement amount ratio falls below the predetermined ratio.

For instance, when the predetermined ratio is set to 10, the movement amount ratio for July 15th and the movement amount ratio for July 20th during the 10 days from July 14th to July 23rd fall below the predetermined ratio. Thus, the frequency of not good days during the 10 days from July 14th to July 23rd is derived by 2/10. That is, the derived frequency is 20%. For instance, when the frequency of not good days during the determination period from July 14th to July 23rd, which is 20%, is higher than the frequency of not good days during the comparison period from July 4th to July 13th, determination unit 122 detects cognitive decline compared with the comparison period.

As discussed above, to determine whether the user has experienced cognitive decline, cognitive decline detection system 120 in the embodiment uses the ratio of the amount of movement during the non-sleep period to the amount of movement during the sleep period. The movement amount ratio can indicate whether the user moves actively during the active period and sleeps well during the sleep period. By using such a movement amount ratio, cognitive decline detection system 120 can properly determine whether the user has experienced cognitive decline.

Furthermore, to determine whether the user has experienced cognitive decline, cognitive decline detection system 120 in the embodiment uses the frequency of days when the movement amount ratio falls below the predetermined ratio. For instance, even if the user has experienced no cognitive decline, the movement amount ratio may vary from day to day, and the movement amount ratio for a day the user has less tasks may fall below the predetermined ratio. However, even if the movement amount ratio varies from day to day, by using the frequency of days when the movement amount ratio falls below the predetermined ratio, cognitive decline detection system 120 can properly determine whether the user has experienced cognitive decline.

Variation

To determine whether the user has experienced cognitive decline, cognitive decline detection system 120 in the disclosed embodiment uses the frequency of days when the movement amount ratio falls below the predetermined ratio. Instead of the frequency of days when the movement amount ratio falls below the predetermined ratio, cognitive decline detection system 120 may use the value of the slope of an approximation straight line for a ratio change represented by movement amount ratios for respective days.

Hereinafter, as a variation, an instance is described in which the value of the slope of an approximation straight line for a ratio change represented by movement amount ratios for respective days is used instead of the frequency of days when the movement amount ratio falls below the predetermined ratio. It should be noted that the approximation straight line may be referred to as movement-amount-ratio approximation straight line. In addition, the configuration of cognitive decline detection system 120 and other devices in the variation are the same as that of the corresponding system and devices illustrated in the example in FIG. 3. However, operation of cognitive decline detection system 120 and other devices in the variation partly differs from that of the corresponding system and devices illustrated in the example in FIG. 4.

Figure 8:
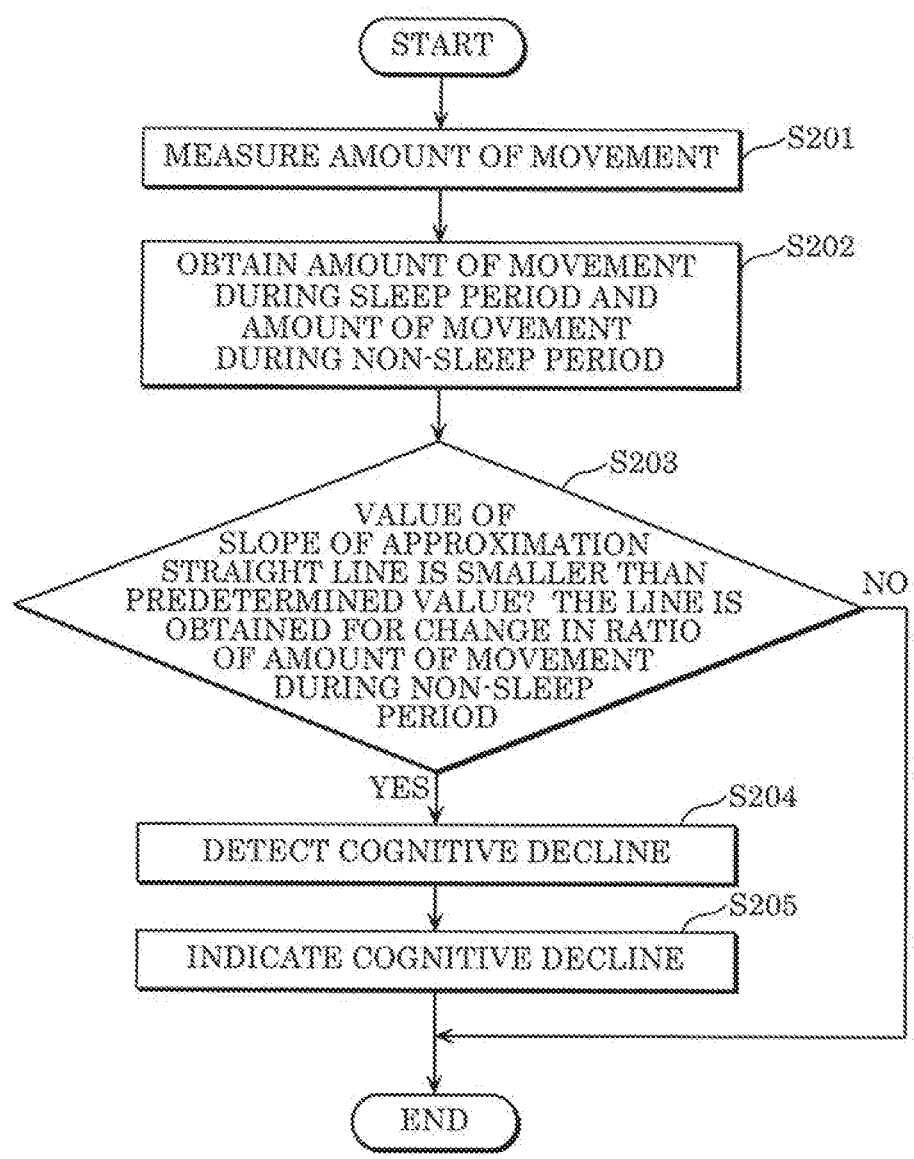
FIG. 8 is a flowchart illustrating operation of a cognitive decline detection system and other devices in a variation.

FIG. 8 is a flowchart illustrating operation of cognitive decline detection system 120 and other devices in the variation.

As in the case of the measuring (S101) in FIG. 4, measurement unit 110 measures the amount of movement of a user (S201). For instance, measurement unit 110 measures the amounts of movement of the user at one-minute intervals.

As in the case of the obtaining (S102) in FIG. 4, obtainment unit 121 obtains the amount of movement during the sleep period and the amount of movement during the non-sleep period (S202). For instance, obtainment unit 121 separates the amounts of movement measured at one-minute intervals into the amount of movement during the sleep period and the amount of movement during the non-sleep period, which are then accumulated for each day. Thus, obtainment unit 121 obtains the amount of movement during the sleep period and the amount of movement during the non-sleep period for each day.

Determination unit 122 determines whether the value of the slope of an approximation straight line falls below a predetermined value of a slope (S203), the approximation straight line being obtained for a ratio change represented by movement amount ratios for respective days, and the movement amount ratios each representing the ratio of the amount of movement during the non-sleep period to the amount of movement during the sleep period. That is, determination unit 122 determines whether the value of the slope of the movement-amount-ratio approximation straight line for a determination period falls below the predetermined value of the slope. While extending the determination period for one day each day, determination unit 122 may determine whether the value of the slope of the movement-amount-ratio approximation straight line for a current determination period falls below the predetermined value of the slope.

Determination unit 122 detects cognitive decline (S204) when the value of the slope of the approximation straight line falls below the predetermined value of the slope (Yes in S203), the approximation straight line being obtained for the ratio change represented by the movement amount ratios for the respective days, and the movement amount ratios each representing the ratio of the amount of movement during the non-sleep period to the amount of movement during the sleep period.

That is, when the value of the slope of the movement-amount-ratio approximation straight line for the determination period falls below the predetermined value of the slope, determination unit 122 detects cognitive decline during the determination period. That is, in this instance, determination unit 122 determines that cognitive function is lower in the latter part of the determination period than in the first part of the determination period. More specifically, in this instance, determination unit 122 may determine that cognitive function is lower on the final day of the determination period than on the first day of the determination period.

Notification unit 130 indicates cognitive decline (S205) when the value of the slope of the approximation straight line falls below the predetermined value of the slope (Yes in S203), the approximation straight line being obtained for the ratio change represented by the movement amount ratios for the respective days, and the movement amount ratios each representing the ratio of the amount of movement during the non-sleep period to the amount of movement during the sleep period. That is, when the value of the slope of the movement-amount-ratio approximation straight line for the determination period falls below the predetermined value of the slope, notification unit 130 indicates cognitive decline during the determination period.

In the above operation, cognitive decline detection system 120 can properly detect cognitive decline in accordance with the value of the slope of the approximation straight line for the ratio change represented by the movement amount ratios for the respective days, the movement amount ratios each representing the ratio of the amount of movement during the non-sleep period to the amount of movement during the sleep period.

When the value of the slope of the approximation straight line for the ratio change does not fall below the predetermined value of the slope (No in S203), determination unit 122 may determine that the user has experienced no cognitive decline. In this case, notification unit 130 may indicate that the user has experienced no cognitive decline.

In addition, for instance, the predetermined value of the slope, which is compared with the value of the slope of a movement-amount-ratio approximation straight line for a determination period, may be set to zero. When the value of the slope of a movement-amount-ratio approximation straight line for a determination period is a negative value, it is likely that the movement amount ratio is lower in the latter part of the determination period than in the first part of the determination period. Thus, when the value of the slope of the movement-amount-ratio approximation straight line for the determination period falls below zero, determination unit 122 may determine that cognitive function is lower in the latter part of the determination period than in the first part of the determination period.

The predetermined value of the slope may be smaller than zero and, for example, a negative value within a permissible range. The predetermined value of the slope may be set in accordance with the value of the slope of a movement-amount-ratio approximation straight line for a past period.

Moreover, for example, as night becomes longer from fall to winter, time available for activities decreases. In addition, since it gets cold from fall to winter, the amount of movement during the time available for activities is likely to decrease. Thus, even if the user has experienced no cognitive decline, the amount of movement during the non-sleep period may decrease, and consequently, the ratio of the amount of movement during the non-sleep period to the amount of movement during the sleep period may decrease. That is, even if the user has experienced no cognitive decline, due to the season or other factors, the value of the slope of the movement-amount-ratio approximation straight line may indicate a value of a slope smaller than zero.

Thus, the predetermined value of the slope may be set in accordance with the value of the slope of a movement-amount-ratio approximation straight line for the same season in the past. More specifically, the value of the slope of the movement-amount-ratio approximation straight line for the period exactly one year before the determination period may be used as the predetermined value of the slope. For instance, when the determination period is from Sep. 1, 2016 to Dec. 31, 2016, the value of the slope of a movement-amount-ratio approximation straight line for the period from Sep. 1, 2015 to Dec. 31, 2015 may be used as the predetermined value of the slope.

Moreover, as the same season in the past, in addition to the period one year before the determination period, a period two years or more than two years before the determination period may be used. That is, a corresponding period may be used. The corresponding period is before the determination period, and the corresponding period and the determination period are identical periods of different years. The value of the slope of a movement-amount-ratio approximation straight line for such a corresponding period may be used as the predetermined value of the slope. It should be noted that the same season of different years may be used instead of the same period of different years.

In the above operation, the condition of whether the value of the slope of an approximation straight line falls below the predetermined value is used, the approximation straight line being obtained for a change in the ratio of the amount of movement during the non-sleep period to the amount of movement during the sleep period. By using other substantially the same condition as the condition, the condition of whether the value of the slope of an approximation straight line falls below the predetermined value may be used, the approximation straight line being obtained for a change in the ratio of the amount of movement during the non-sleep period to the amount of movement during the sleep period.

Specifically, by using the condition of whether the value of the slope of an approximation straight line for a change in the ratio of the amount of movement during the non-sleep period to the total amount of movement falls below the predetermined value, the condition of whether the value of the slope of an approximation straight line for a change in the ratio of the amount of movement during the non-sleep period to the amount of movement during the sleep period falls below the predetermined value may be used. Alternatively, by using the condition of whether the value of the slope of an approximation straight line for a change in the ratio of the amount of movement during the non-sleep period to the amount of movement during the sleep period is greater than the predetermined value, the condition of whether the value of the slope of an approximation straight line for a change in the ratio of the amount of movement during the non-sleep period to the amount of movement during the sleep period falls below the predetermined value may be used.

Figure 9:
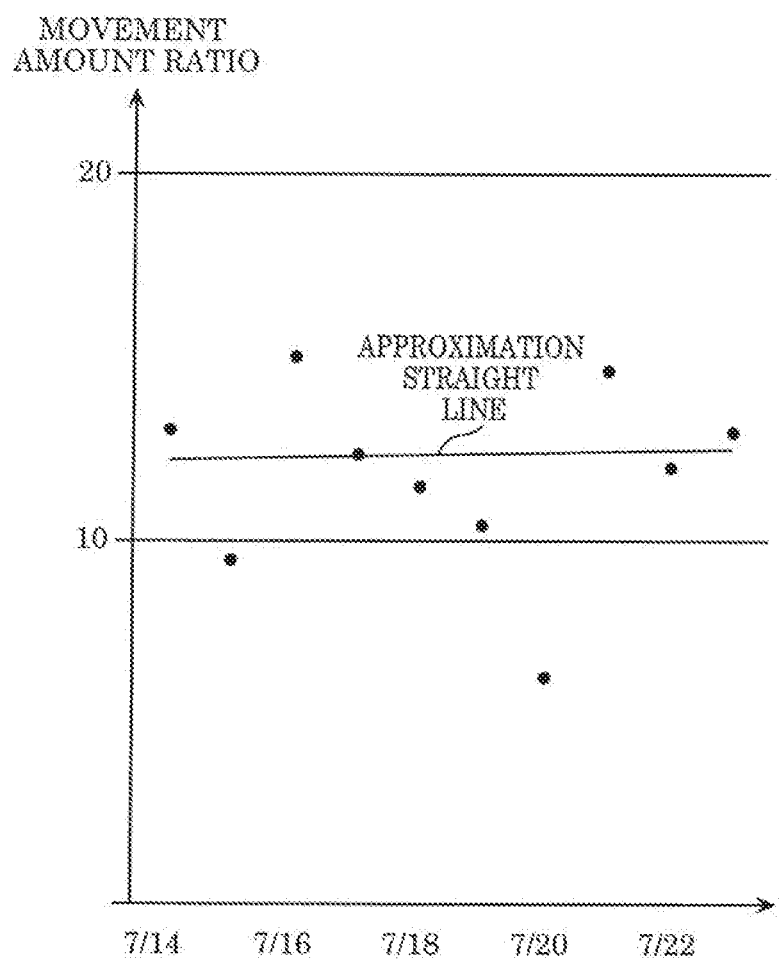
FIG. 9 is a graph illustrating an approximation straight line for a change in the movement amount ratio.

FIG. 9 is a graph illustrating an approximation straight line for a change in the movement amount ratio. Specifically, the movement-amount-ratio approximation straight line is added to the graph illustrated in FIG. 7. The movement-amount-ratio approximation straight line is an approximation straight line for a ratio change represented by movement amount ratios for respective days. In accordance with the value of the slope of the movement-amount-ratio approximation straight line, cognitive decline detection system 120 determines whether the user has experienced cognitive decline.

For instance, when the value of the slope of the movement-amount-ratio approximation straight line falls below the predetermined value of the slope, cognitive decline detection system 120 detects cognitive decline. Specifically, when the predetermined value of the slope is zero, and the value of the slope of the movement-amount-ratio approximation straight line falls below zero, cognitive decline detection system 120 may detect cognitive decline.

For instance, when the value of the slope of the movement-amount-ratio approximation straight line is greater than the predetermined value of the slope, cognitive decline detection system 120 determines that the user has experienced no cognitive decline. Specifically, when the predetermined value of the slope is zero, and the value of the slope of the movement-amount-ratio approximation straight line does not fall below zero, cognitive decline detection system 120 may determine that the user has experienced no cognitive decline.

As discussed above, to determine whether the user has experienced cognitive decline, cognitive decline detection system 120 in the variation uses the value of the slope of an approximation straight line for a ratio change represented by movement amount ratios for respective days, the movement amount ratios each representing the ratio of the amount of movement during the non-sleep period to the amount of movement during the sleep period. When the value of the slope of the approximation straight line falls below the predetermined value, such as zero, due to the circadian rhythm sleep disorders, the amount of movement during the daytime is likely to decrease, and the amount of movement during the night-time is likely to increase.

Thus, cognitive decline detection system 120 can properly determine whether the user has experienced cognitive decline, by using the value of the slope of an approximation straight line.

Thus, cognitive decline detection system 120 in one aspect of the present invention is described in accordance with the embodiment and the variation. However, the present invention is not limited to the disclosed embodiment and variation. The present invention covers: an embodiment obtained by making changes conceived by those skilled in the art to the embodiment and/or the variation; and another embodiment created by optionally combining structural elements described in the embodiment and/or the variation.

For instance, a processing task performed by a specific structural element may be performed by another structural element. The order of processing tasks may be changed or more than one processing task may be performed in parallel.

In addition, each day for which, for example, the amount of movement during the sleep period, the amount of movement during the non-sleep period, and the movement amount ratio are obtained does not have to start from 12 a.m. For instance, 24 hours from 12 p.m. to 12 p.m. next day may be specified as one day.

In addition, the present invention may be cognitive decline detection system 120 and a cognitive decline detection method, the method including steps performed by the structural elements of cognitive decline detection system 120. For instance, the steps are performed by a computer system including a processor, memory, and an input and output circuit. The present invention may be a program that the computer system runs to perform the steps included in the method. It should be noted that the computer system may be simply referred to as computer.

Moreover, the present invention can be realized as a non-transitory computer-readable recording medium on which the program is recorded. The recording medium may be an optical disk, such as CD-ROM, a magnetic disk, such as a hard disk drive, a magneto-optical (MO) disk, semiconductor memory, such as flash memory, or other non-transitory computer-readable recording medium. Moreover, the program may be pre-recorded on the recording medium or recorded on the recording medium by supplying the program to the recording medium via a communication network.

For instance, when the present invention is a program, the steps are performed by running the program by using hardware resources such as the processor, the memory, and the input and output circuit of the computer system. That is, the steps are performed as a result of the processor obtaining data from, for instance, the memory or the input and output circuit and performing a computation and as a result of the processor outputting the result of the computation to, for example, the memory or the input and output circuit. Any type of processor may be used as a processor for running the program.

Moreover, each of the structural elements of cognitive decline detection system 120 may be a dedicated or general-purpose circuit. The structural elements may constitute one circuit or more than one circuit.

The structural elements of cognitive decline detection system 120 may be integrated into a large scale integration (LSI), which is an integrated circuit (IC). The structural elements may be made as individual chips, or a part or all of the structural elements may be integrated into one chip. The structural elements may be included in at least one chip of a device or may be included in more than one chip of more than one device.

Moreover, according to the degree of integration, LSI may be referred to as system LSI, super LSI or ultra LSI. Moreover, the integrated circuit may be a dedicated circuit or a general-purpose processor. A field programmable gate array (FPGA) that can be programmed or a reconfigurable processor that enables re-configuration of connection and setting of internal circuit cells may be used.

Furthermore, with advancement of the semiconductor technology or advent of another derivative technology, a new circuit integration technology that will replace LSI may be developed. If this is the case, of course, by using the new technology, circuit integration of the structural elements of cognitive decline detection system 120 may be performed.

Hereinafter, aspects of cognitive decline detection system 120 and the program are described as examples. Theses aspects may be appropriately combined. In addition, elements such as the optional structural elements disclosed in the embodiment and the variation may be added.

(First Aspect)

Cognitive decline detection system 120 according to one aspect of the present invention includes obtainment unit 121 and determination unit 122. Obtainment unit 121 obtains the amount of movement during a sleep period and the amount of movement during a non-sleep period of a user for each day. The non-sleep period is the period other than the sleep period.

When the frequency of days when a movement amount ratio falls below a predetermined ratio among days constituting a determination period is higher than the frequency of days when the movement amount ratio falls below the predetermined ratio among days constituting a comparison period, determination unit 122 determines that the cognitive function of the user is lower during the determination period than during the comparison period. Here, the movement amount ratio represents the ratio of the amount of movement during the non-sleep period to the amount of movement during the sleep period. The comparison period is before the determination period.

Thus, to determine whether the user has experienced cognitive decline, cognitive decline detection system 120 uses the ratio of the amount of movement during the non-sleep period to the amount of movement during the sleep period. For instance, when the user has experienced cognitive decline, due to the circadian rhythm sleep disorders, the user is likely to have light sleep during the night-time and be less active during the daytime. Thus, the movement amount ratio is likely to decrease. Accordingly, in accordance with the cognitive-decline related characteristics, cognitive decline detection system 120 can properly determine whether the user has experienced cognitive decline.

In addition, to determine whether the user has experienced cognitive decline, cognitive decline detection system 120 uses the frequency of days when the movement amount ratio falls below the predetermined ratio. Thus, it is possible to suppress cognitive decline detection system 120 from improperly determining a temporary decline in the movement amount ratio not due to cognitive decline, as cognitive decline.

(Second Aspect)

For instance, the predetermined ratio may be set in accordance with a statistic derived from movement amount ratios for the respective days of the reference period, which is before the comparison period. Thus, cognitive decline detection system 120 can properly evaluate movement amount ratios in accordance with the past movement amount ratios.

(Third Aspect)

For instance, the predetermined ratio may be a value derived by subtracting the standard deviation of the movement amount ratios from the mean value of the movement amount ratios. Thus, cognitive decline detection system 120 can properly evaluate movement amount ratios in accordance with the average range derived from the past movement amount ratios.

(Fourth Aspect)

For instance, when the frequency of not good days during the comparison period is lower than or equal to a predetermined frequency, and the frequency of not good days during the determination period is higher than the predetermined frequency, determination unit 122 may determine that the cognitive function of the user is lower during the determination period than during the comparison period. Here, the frequency of not good days during the comparison period represents the frequency of days when the movement amount ratio falls below the predetermined ratio among the days constituting the comparison period. The frequency of not good days during the determination period represents the frequency of days when the movement amount ratio falls below the predetermined ratio among the days constituting the determination period.

Thus, when the frequency of not good days is beyond the permissible range, cognitive decline detection system 120 can determine that the cognitive function decreases to an abnormally low level.

(Fifth Aspect)

For instance, cognitive decline detection system 120 may further include notification unit 130. When cognitive decline is detected, notification unit 130 may indicate cognitive decline. Thus, when the user has experienced cognitive decline, cognitive decline detection system 120 may notify cognitive decline to, for example, the caregiver of the user.

(Sixth Aspect)

For instance, cognitive decline detection system 120 may further include measurement unit 110. Measurement unit 110 may measure the amount of movement of the user. Obtainment unit 121 may obtain the amount of movement measured by measurement unit 110. Obtainment unit 121 may identify the sleep period for each day in accordance with the amount of movement measured by measurement unit 110. Obtainment unit 121 may obtain the amount of movement during the sleep period and the amount of movement during the non-sleep period for each day in accordance with the amount of movement measured by measurement unit 110 and the sleep period for each day.

Thus, cognitive decline detection system 120 can properly identify the sleep period in accordance with the amount of movement of the user. Thus, cognitive decline detection system 120 can properly obtain the amount of movement during the sleep period and the amount of movement during the non-sleep period, which is the period other than the sleep period. Thus, cognitive decline detection system 120 can properly determine whether the user has experienced cognitive decline in accordance with the amount of movement during the sleep period and the amount of movement during the non-sleep period, which are properly obtained.

(Seventh Aspect)

Cognitive decline detection system 120 according to another aspect of the present invention includes obtainment unit 121 and determination unit 122. Obtainment unit 121 obtains the amount of movement during a sleep period and the amount of movement during a non-sleep period of a user. The non-sleep period is the period other than the sleep period. When the value of the slope of an approximation straight line falls below a predetermined value of a slope, determination unit 122 detects cognitive decline in the user during a determination period. The approximation straight line is obtained for a ratio change represented by movement amount ratios for the respective days of the determination period, the movement amount ratios each representing the ratio of the amount of movement during the non-sleep period to the amount of movement during the sleep period.

Thus, to determine whether the user has experienced cognitive decline, cognitive decline detection system 120 uses the ratio of the amount of movement during the non-sleep period to the amount of movement during the sleep period. For instance, when the user has experienced cognitive decline, due to the circadian rhythm sleep disorders, the user is likely to have light sleep during the night-time and be less active during the daytime. Thus, the movement amount ratio is likely to decrease. Accordingly, in accordance with the cognitive-decline related characteristics, cognitive decline detection system 120 can properly determine whether the user has experienced cognitive decline.

Furthermore, to determine whether the user has experienced cognitive decline, cognitive decline detection system 120 uses the value of the slope of the approximation straight line for the ratio change represented by the movement amount ratios for the respective days of the determination period. When the value of the slope of the approximation straight line falls below the predetermined value of the slope, due to the circadian rhythm sleep disorders, the amount of movement during the daytime is likely to decrease, and the amount of movement during the night-time is likely to increase. Thus, by using the value of the slope of an approximation straight line, cognitive decline detection system 120 can properly determine whether the user has experienced cognitive decline.

(Eighth Aspect)

For instance, the predetermined value of the slope may be the value of the slope of an approximation straight line for a ratio change represented by movement amount ratios for the respective days of a corresponding period. Here, the corresponding period is before the determination period, and the corresponding period and the determination period are identical periods of different years.

Thus, when the value of the slope for the determination period falls below the value of the slope for the same period in the past, cognitive decline detection system 120 can detect cognitive decline. Thus, to determine whether the user has experienced cognitive decline, cognitive decline detection system 120 can reflect, for example, the characteristics of the season.

(Ninth Aspect)

For instance, cognitive decline detection system 120 may further include notification unit 130. When cognitive decline is detected, notification unit 130 may indicate cognitive decline. Thus, when the user has experienced cognitive decline, cognitive decline detection system 120 can notify cognitive decline to, for example, the caregiver of the user.

(Tenth Aspect)

For instance, cognitive decline detection system 120 may further include measurement unit 110. Measurement unit 110 may measure the amount of movement of the user. Obtainment unit 121 may obtain the amount of movement measured by measurement unit 110. Obtainment unit 121 may identify the sleep period for each day in accordance with the amount of movement measured by measurement unit 110. Obtainment unit 121 may obtain the amount of movement during the sleep period and the amount of movement during the non-sleep period for each day in accordance with the amount of movement measured by measurement unit 110 and the sleep period identified for each day.

Thus, cognitive decline detection system 120 can properly identify the sleep period in accordance with the amount of movement of the user. Thus, cognitive decline detection system 120 can properly obtain the amount of movement during the sleep period and the amount of movement during the non-sleep period, which is the period other than the sleep period. Thus, cognitive decline detection system 120 can properly determine whether the user has experienced cognitive decline, in accordance with the amount of movement during the sleep period and the amount of movement during the non-sleep period, which are properly obtained.

(Eleventh Aspect)

A program according to another aspect of the present invention is a program that a computer runs to perform a cognitive decline detection method. The cognitive decline detection method includes obtaining (S102) and determining (S103, S104). In the obtaining (S102), the amount of movement during a sleep period and the amount of movement during a non-sleep period of a user are obtained for each day. The non-sleep period is the period other than the sleep period.

In the determining (S103, S104), when the frequency of not good days is higher during the determination period than during the comparison period, it is determined that the cognitive function of the user is lower during a determination period than during a comparison period.

Here, the frequency of not good days during the determination period represents the frequency of days when a movement amount ratio falls below a predetermined ratio among days constituting the determination period. The frequency of not good days during the comparison period represents the frequency of days when the movement amount ratio falls below the predetermined ratio among days constituting the comparison period. The movement amount ratio represents the ratio of the amount of movement during the non-sleep period to the amount of movement during the sleep period. The comparison period is before the determination period.

Thus, by running the program, the computer can perform the cognitive decline detection method for determining whether the user has experienced cognitive decline by using the frequency of days when the movement amount ratio falls below the predetermined ratio, the movement amount ratio representing the ratio of the amount of movement during the non-sleep period to the amount of movement during the sleep period. Thus, by running the program, it is possible to obtain effects similar to those obtained by cognitive decline detection system 120 that determines whether the user has experienced cognitive decline by using the frequency of days when the movement amount ratio falls below the predetermined ratio, the movement amount ratio representing the ratio of the amount of movement during the non-sleep period to the amount of movement during the sleep period.

(Twelfth Aspect)

A program according to another aspect of the present invention is a program that a computer runs to perform a cognitive decline detection method. The cognitive decline detection method includes obtaining (S202) and determining (S203, S204). In the obtaining (S202), the amount of movement during a sleep period and the amount of movement during a non-sleep period of a user are obtained for each day. The non-sleep period is the period other than the sleep period.

In the determining (S203, S204), when the value of the slope of an approximation straight line falls below a predetermined value of a slope, it is determined that the cognitive function of the user is lower in days included in the latter part of a determination period than in days included in the first part of the determination period. The approximation straight line is obtained for a ratio change represented by movement amount ratios for the respective days of the determination period. Here, the movement amount ratios each represent the ratio of the amount of movement during the non-sleep period to the amount of movement during the sleep period.

Thus, by running the program, the computer can perform the cognitive decline detection method for determining whether the user has experienced cognitive decline by using the value of the slope of an approximation straight line for a ratio change represented by movement amount ratios for respective days, the movement amount ratios each representing the amount of movement during the non-sleep period to the amount of movement during the sleep period. Thus, by running the program, it is possible to obtain effects similar to those obtained by cognitive decline detection system 120 that determines whether the user has experienced cognitive decline by using the value of the slope of an approximation straight line for a ratio change represented by movement amount ratios for respective days, the movement amount ratios each representing the ratio of the amount of movement during the non-sleep period to the amount of movement during the sleep period.

REFERENCE MARKS IN THE DRAWINGS

110 measurement unit
120 cognitive decline detection system
121 obtainment unit
122 determination unit
130 notification unit

The invention claimed is:

1. A cognitive decline detection system, comprising:
a processor; and
memory accessible by the processor,
wherein the processor:

obtains, from a measurement device, an amount of movement during a sleep period and an amount of movement during a non-sleep period of a user for each day, the non-sleep period being a period other than the sleep period;
stores the amount of movement during the sleep period and the amount of movement during the non-sleep period in the memory;
calculates a movement amount ratio for each day, the movement amount ratio representing a ratio of the amount of movement during the non-sleep period to the amount of movement during the sleep period;
calculates a frequency of days when the movement amount ratio falls below a predetermined ratio among days constituting a determination period;
calculates a frequency of days when the movement amount ratio falls below the predetermined ratio among days constituting a comparison period set before the determination period;
determines that cognitive function of the user is lower during the determination period than during the comparison period when the frequency of days when the movement amount ratio falls below the predetermined ratio among the days constituting the determination period is higher than the frequency of days when the movement amount ratio falls below the predetermined ratio among the days constituting the comparison period; and
notifies, by a speaker or a display, a determination result indicating that the cognitive function is lower during the determination period than during the comparison period, and
the predetermined ratio is set in accordance with a statistic derived from movement amount ratios for respective days of a reference period set before the comparison period, each of the movement amount ratios being the movement amount ratio.

2. The cognitive decline detection system according to claim 1,
wherein the predetermined ratio is derived by subtracting a standard deviation of the movement amount ratios from a mean value of the movement amount ratios.

3. The cognitive decline detection system according to claim 1,
wherein the processor detects a decline in the cognitive function when the frequency of days when the movement amount ratio falls below the predetermined ratio among the days constituting the comparison period is lower than or equal to a predetermined frequency, and the frequency of days when the movement amount ratio falls below the predetermined ratio among the days constituting the determination period is higher than the predetermined frequency.

4. The cognitive decline detection system according to claim 1,
wherein the measurement device measures an amount of movement of the user, and
the processor:
obtains the amount of movement measured by the measurement device;
identifies the sleep period for each day in accordance with the amount of movement measured by the measurement device; and
obtains the amount of movement during the sleep period and the amount of movement during the non-sleep period for each day in accordance with the amount of movement measured by the measurement device and the sleep period identified for each day.

5. A cognitive decline detection system, comprising:
a processor; and
memory accessible by the processor,
wherein the processor:
obtains, from a measurement device, an amount of movement during a sleep period and an amount of movement during a non-sleep period of a user for each day, the non-sleep period being a period other than the sleep period;
stores the amount of movement during the sleep period and the amount of movement during the non-sleep period in the memory;
calculates a movement amount ratio for each day, the movement amount ratio representing a ratio of the amount of movement during the non-sleep period to the amount of movement during the sleep period;
determines that the user has experienced a decline in cognitive function during a determination period when a value of a slope of an approximation straight line falls below a predetermined value of a slope, the approximation straight line being obtained for a ratio change represented by movement amount ratios for respective days of the determination period, each of the movement amount ratios being the movement amount ratio; and
notifies, by a speaker or a display, a determination result indicating that the user has experienced a decline in cognitive function during the determination period,
the predetermined value of the slope is a value of a slope of an approximation straight line for a ratio change represented by movement amount ratios for respective days of a corresponding period, and
the corresponding period is before the determination period, and the corresponding period and the determination period are identical periods of different years.

6. The cognitive decline detection system according to claim 5,
wherein the measurement device measures an amount of movement of the user, and
the processor:
obtains the amount of movement measured by the measurement device;
identifies the sleep period for each day in accordance with the amount of movement measured by the measurement device; and
obtains the amount of movement during the sleep period and the amount of movement during the non-sleep period for each day in accordance with the amount of movement measured by the measurement device and the sleep period identified for each day.

7. A non-transitory computer-readable recording medium for use in a computer including a processor and memory, the recording medium having a computer program recorded thereon for causing the computer to perform a cognitive decline detection method,
wherein in the cognitive decline detection method, the processor:
obtains, from a measurement device, an amount of movement during a sleep period and an amount of movement during a non-sleep period of a user for each day, the non-sleep period being a period other than the sleep period;

stores the amount of movement during the sleep period and the amount of movement during the non-sleep period in the memory;

calculates a movement amount ratio for each day, the movement amount ratio representing a ratio of the amount of movement during the non-sleep period to the amount of movement during the sleep period;

calculates a frequency of days when the movement amount ratio falls below a predetermined ratio among days constituting a determination period;

calculates a frequency of days when the movement amount ratio falls below the predetermined ratio among days constituting a comparison period set before the determination period;

determines that cognitive function of the user is lower during the determination period than during the comparison period when the frequency of days when the movement amount ratio falls below the predetermined ratio among the days constituting the determination period is higher than the frequency of days when the movement amount ratio falls below the predetermined ratio among the days constituting the comparison period; and notifies, by a speaker or a display, a determination result indicating that the cognitive function is lower during the determination period than during the comparison period, and the predetermined ratio is set in accordance with a statistic derived from movement amount ratios for respective days of a reference period set before the comparison period, each of the movement amount ratios being the movement amount ratio.

8. A non-transitory computer-readable recording medium for use in a computer including a processor and memory, the recording medium having a computer program recorded thereon for causing the computer to perform a cognitive decline detection method, wherein in the cognitive decline detection method, the processor:

obtains, from a measurement device, an amount of movement during a sleep period and an amount of movement during a non-sleep period of a user for each day, the non-sleep period being a period other than the sleep period;

stores the amount of movement during the sleep period and the amount of movement during the non-sleep period in the memory;

calculates a movement amount ratio for each day, the movement amount ratio representing a ratio of the amount of movement during the non-sleep period to the amount of movement during the sleep period;

determines that the user has experienced a decline in cognitive function during a determination period when a value of a slope of an approximation straight line falls below a predetermined value of a slope, the approximation straight line being obtained for a ratio change represented by movement amount ratios for respective days of the determination period, each of the movement amount ratios being the movement amount ratio; and notifies, by a speaker or a display, a determination result indicating that the user has experienced a decline in cognitive function during the determination period, the predetermined value of the slope is a value of a slope of an approximation straight line for a ratio change represented by movement amount ratios for respective days of a corresponding period, and the corresponding period is before the determination period, and the corresponding period and the determination period are identical periods of different years.

* * * * *